VARIETY OF LINDEN TREE
Filed June 27, 1974 2 Sheets-Sheet 1
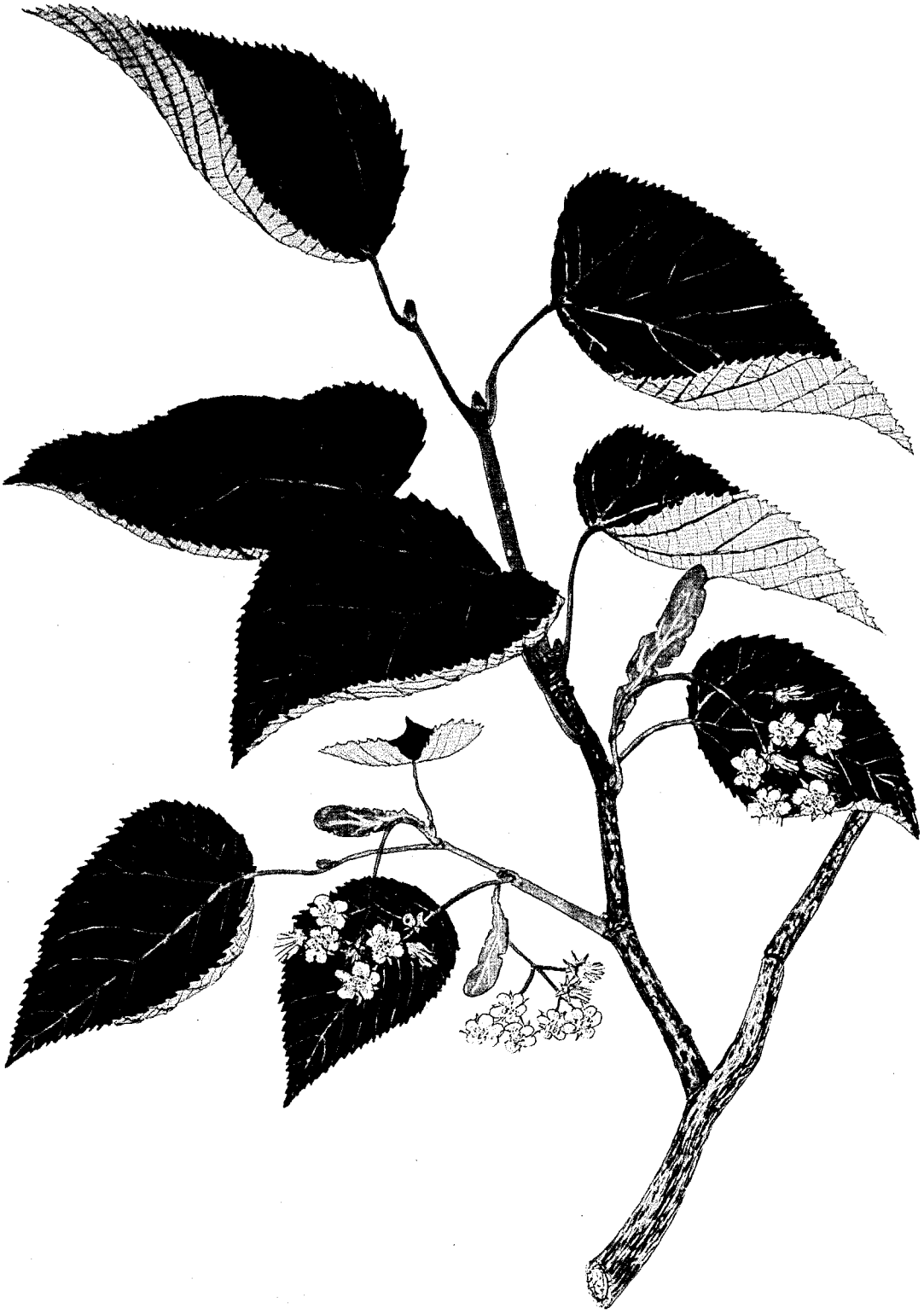

VARIETY OF LINDEN TREE
Filed June 27, 1974 2 Sheets-Sheet 2
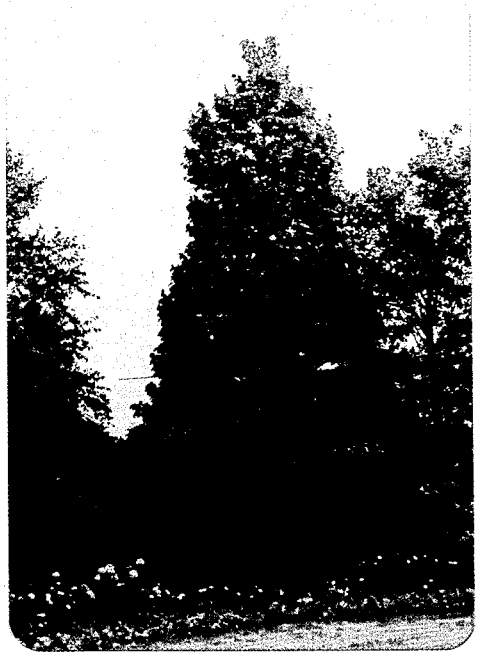

United States Patent

Plant Pat. 3,770
Patented Aug. 26, 1975

3,770

VARIETY OF LINDEN TREE

Willet N. Wandell, Rte. 3, Myra Station Road, Urbana, Ill. 61801

Filed June 27, 1974, Ser. No. 483,876
Int. Cl. A01h *5/12*
U.S. Cl. Plt.—51 1 Claim

This invention relates to a new and distinct variety of the linden tree. The new variety was discovered in a shipment of seedlings of lindens (Tilia) which were planted in a nursery at rural Urbana, Ill.

The new variety was removed from the growing block and used as a screen planting on the nursery premises. The new characteristics were noted prior to transplanting, and distinctive characteristics continued to develop as the new variety grew. Such characteristics generally include vigorous, compact upright growth without requiring any pruning or shaping. The leaves were sizeable, abundant and closely spaced, but did not impart to the tree a coarse or rough appearance.

Many lindens growing in rural Urbana take on a discolored "worn" appearance beginning in August and continuing throughout the fall. The new variety linden tree did not assume such a "worn" appearance, and displayed an outstandingly attractive foliage throughout the summer months and the months of fall, at which time the foliage changed to a bright yellow. The mature tree grows to a height of about 22 ft. after 13 growing seasons.

It is a primary object of the present invention to provide a new and distinct variety of linden trees having the desirable characteristics referred to above and to be described in detail below. Other objects and advantages of the invention will become apparent from the following detailed description taken in conjunction with the accompanying illustrations, in which:

FIG. 1 is an illustration of the foliage with flowering; and

FIG. 2 is an illustration of the new variety after about 13 growing seasons.

The distinguishing characterics are summarized by the improved vigorous, narrow, upright growth which exceeds other growing lindens in the Urbana, Ill. area; the compact growth habit without requiring trimming, pruning and shaping, the attractive dark green leaves which are distinctly lighter at the undersurface, and the foliage which "wears well" throughout the summer growing season, including displaying a bright yellow color in the fall.

The parentage of the new variety is a seedling with characters intermediate *Tilia heterophylla* Vent and *Tilia monticola* Sarg. The new variety is propagated by budding and the propagated tree holds its distinguishing characteristics.

The tree is of medium height, about 22 ft. after 13 growing seasons. The tree is upright, oval-pyramidal and hardy. The trunk is deeply furrowed, the branches are slender and glabrous. The lenticels are sparse. The tree color is medium green, No. 144A on Royal Horticultural Colour Chart, publishd by the Royal Horticultural Society of London, Library Calling No. 581.4, B 77H.

The foliage is described in relation to its leaves, petioles, flowers and fruit.

LEAVES

The leaves are of simple configuration, pinately veined and the leaves range from 9–15 cm. in length and from 7–10 cm. in width. The shape is ovate to oblong-ovate. The apex of the leaf is gradually narrowed and acuminate. The base of the leaf is extremely oblique and truncate or obliquely cordate. The margin of the leaf is finely serrate with straight or incurved apiculate teeth. The color of the leaves is dark green above, No. 147A, greyed-green beneath, No. 191C, and the leaves change in autumn to a bright yellow, No. 3B. The pubescence of the leaves is characterized by being glabrous above to tomentose beneath with tufts of light brown hair in axils of veins.

PETIOLES

The petioles have a length from 3.5–5.24 cm. and are glabrous.

FLOWERS

Flowers are present in axillary and terminal 7–13 flowered cymes. The flowers are fragrant. The flowers have a soft yellow color, No. 8C.

FRUIT

The fruit is dry and woody, indehiscent and globular. Each blossom bears a single fruit, the stalk of the fruit is about 3 cm. in length.

What is claimed is:

1. A new and distinct variety of linden tree substantially as herein shown and described, characterized particularly by the unique combination of vigorous upright growing habit with dense, heavy, compact foliage, attaining a compact form without pruning or trimming, and having foliage dark green above and lighter green below, which foliage is maintained in excellent condition throughout the growing season and which turns to a bright yellow in the fall.

No references cited.

ROBERT E. BAGWILL, Primary Examiner